4,078,060
… Mar. 7, 1978

[54] METHOD OF INDUCING AN ESTROGENIC RESPONSE

[75] Inventors: Harvey D. Benson, Cincinnati; Joyce Francis Grunwell, Hamilton; John O'Neal Johnston, Cincinnati, all of Ohio; Vladimir Petrow, Chapel Hill, N.C.

[73] Assignee: Richardson-Merrell Inc., Wilton, Conn.

[21] Appl. No.: 684,944

[22] Filed: May 10, 1976

[51] Int. Cl.$^2$ ............................................. A61K 31/56
[52] U.S. Cl. ................................... 424/242; 424/243
[58] Field of Search ............................. 424/242, 243

[56] References Cited

U.S. PATENT DOCUMENTS 3,449,381   6/1969   Bowers ............................ 260/397.4

*Primary Examiner*—Elbert L. Roberts
*Attorney, Agent, or Firm*—L. Ruth Hattan; Eugene O. Retter; George W. Rauchfuss, Jr.

[57] ABSTRACT

Compounds of the following general formula are useful in inducing an estrogenic response in a patient in need thereof:

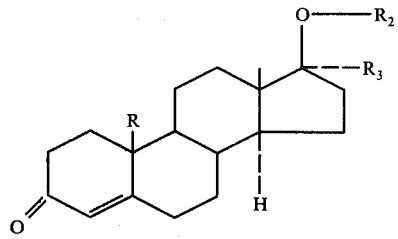

wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$ and R$_3$ together form a double bond between the 17-position carbon atom and the oxygen atom.

7 Claims, No Drawings

METHOD OF INDUCING AN ESTROGENIC RESPONSE

FIELD OF THE INVENTION

This invention relates to methods of inducing an estrogenic response in a patient in need thereof.

BACKGROUND OF THE INVENTION

Steroidal estrogens represent a very important group of biologically active agents which find wide use in both medicine and in veterinary practice where they are employed for a variety of conditions including treatment of hypogonadal women, inhibition of ovulation in women, when they are generally admixed with a progestogen, hormonal support of menopausal and post-menopausal women including treatment of osteoporosis, treatment of acne in men and women, slowing down male pattern baldness in men and women, treatment of atrophic vaginitis, treatment of breast cancer in post-menopausal women and in men, treatment of benign prostatic hypertrophy and prostatic carcinoma in men, chemical caponization of chickens and promoting growth of cattle. In recent years it has become apparent, however, that estrogenic products presently in use possess certain undesirable side effects which must be set against the undoubted benefits resulting from their use. For example, diethylstilbestrol, a once widely used and well established estrogen has been implicated as possibly being responsible for vaginal cancer and adenosis in the female offspring of pregnant women treated with the compound (Lancet 1975, 1960). Also, ethinyl estradiol and mestranol, which represent estrogenic components in current oral contraceptives, are now known to be involved in certain serious side effects associated with oral contraceptives including depression (Nature 243, 58 (1973)), hypertension (Am. J. Obstet. Gynecol. 112, 912 (1972)), carbohydrate and lipid abnormalities (Lancet 1969, October 11, p. 783), interference with blood clotting mechanism resulting in thrombosis and stroke (Ann. Intern. Med. 72, 111 (1970)), and jundice (Am. J. Obstet. Gynecol. 119, 165 (1974)). The use of the above mentioned estrogens or of estradiol, estrone or the sulphated conjugates of estrogens by menopausal and post-menopausal women is often attended by undesirable uterine bleeding and spotting. Also, the administration of estrogens to post-menopausal women has been implicated as a cause of endometrial cancer occurring in such women (Science 191, 838 (1976)). Topical estrogens are used for the treatment of aging skin in women and are known to produce uterine bleeding and spotting at effective dose levels. The use of estrogens for the treatment of acne in women can lead to uterine bleeding and spotting and breast tenderness, and in men, gynecomastia and impotence. The use of estrogens in the treatment of benign prostatic hypertrophy and of prostatic carcinoma in men is known to be associated with a high incidence of fatal thrombosis, gynecomastia and impotence which significantly negates the valuable therapeutic effects of the medication. Consequently there is a need for an improved method of inducing an estrogenic effect in humans and domestic animals in need thereof which will be substantially free of the undesirable side effects associated with estrogen therapy.

SUMMARY OF INVENTION

This invention relates to a method of inducing an estrogenic response in a patient in need thereof by administering a compound of the following general formula:

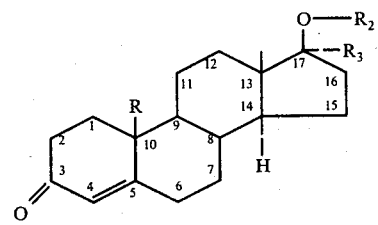

Formula I wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$ and R$_3$ together form a double bond between the 17- position carbon atom and the oxygen atom.

DETAILED DESCRIPTION OF INVENTION

In the compounds of general Formula I the term alkylcarbonyl is taken to mean a group of the structure alkyl

wherein the alkyl moiety has from 1 to 20 carbon atoms and can be a straight chain or a branched chain. Illustrative examples of the alkyl moiety in the substituent alkylcarbonyl group are methyl, ethyl, n-propyl, iso-propyl, n-butyl, sec-butyl, tert-butyl, n-pentyl, neopentyl, pivalyl, hexyl, heptyl, octyl, 2,4-dimethyloctyl, undecyl, 9-methylundecyl, pentadecyl, hexadecyl, dodecyl, 2,4,6-trimethyldecyl, pentadecyl, hexadecyl, dodecyl, 2,4,6-trimethyldecyl, heptadecyl, decyl, octadecyl, nonadecyl and didecyl.

The term benzoyl as used in reference to the compounds of general formula I is taken to mean the group

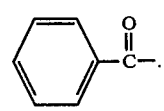

The term phenylalkylcarbonyl as used in reference to the compounds of general formula I is taken to mean a substituent group of the structure

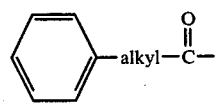

wherein the alkyl moiety, which may also be referred to as an alkylene moiety, has from 1 to 6 carbon atoms and can be a straight chain or a branched chain. Illustrative examples of the alkyl moiety in the substituent phenylalkylcarbonyl group are methyl, ethyl, n-propyl, n-butyl, n-pentyl, hexyl, isopropyl, sec-butyl, tert-butyl and neopentyl.

Illustrative examples of cycloalkylcarbonyl groups which $R_1$ and $R_2$ may be are cyclopentanecarbonyl, cyclohexanecarbonyl, cyclooctanecarbonyl, 1- or 2-norbornanecarbonyl and 1- or 2-adamantanecarbonyl.

It is apparent from the foregoing general Formula I that the compounds employed in the instant invention are androst-4-ene-3,17-diones having a $-CH_2OR_1$ or $-CHO$ group at the 10β-position as represented respectively by the following general Formulas II and III, or are 17β-hydroxyandrost-4-en-3-one derivatives or esters thereof as defined by $R_2$ having a $-CH_2OR_1$ or $-CHO$ group present at the 10β-position as represented respectively by the following general Formulas IV and V:

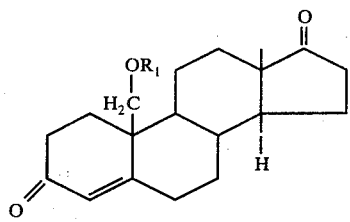

Formula II

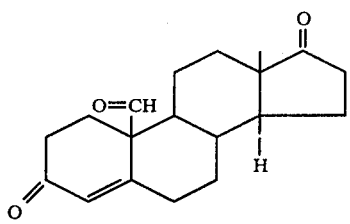

Formula III

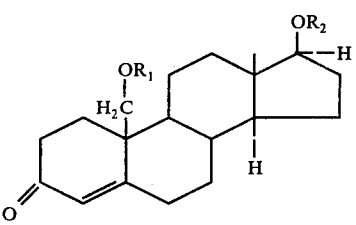

Formula IV

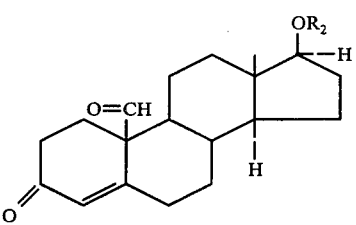

Formula V

In general Formulas II and IV $R_1$ is hydrogen or alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms as defined hereinabove.

In general Formulas IV and V the hydrogen atom attached to the 17-position is in the alpha position, and $R_2$ is hydrogen or alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or, cycloalkylcarbonyl wherein the cycloalkyl moiety has from 5 to 10 carbon atoms as defined hereinabove.

The use of the compounds as represented by each of general Formulas II and III for the purpose of inducing an estrogenic response in a patient in need thereof represent preferred embodiments of this invention with the use of the compounds of general Formula III being a more preferred embodiment. Other embodiments of this invention are the use of the compounds as represented by general Formulas IV and V for the purpose of inducing an estrogenic response in a patient in need thereof with the use of the compounds of general Formula IV wherein $R_1$ and $R_2$ each represent hydrogen and the compounds of general Formula V wherein $R_2$ represents hydrogen being more preferred embodiments.

Illustrative examples of compounds employed in the present invention are 17β,19-bis-(1-oxopropoxy)androst-4-en-3-one, 17β,19-bis-(1-oxodidecyloxy)androst-4-en-3-one, 17β,19-dihydroxyandrost-4-en-3-one, 19-hydroxy-17β-(1-oxopropoxy)androst-4-en-3-one, 19-hydroxy-17β-(1-oxohexadecyloxy)androst-4-en-3-one, 19-acetoxyandrost-4-ene-3,17-dione, 19-acetoxy-17β-hydroxyandrost-4-en-3-one, 3-oxo-17β-hydroxyandrost-4-en-19-al, 19-(1-adamantanylcarbonyloxy)androst-4-ene-3,17-dione, 19-(1-norbornylcarbonyloxy)-androst-4-ene-3,17-dione, 19-(1-cyclopentylcarbonyloxy)-androst-4-ene-3,17-dione, 3,17-dioxoandrost-4-en-19-al and 3-oxo-17β-(1-adamantanylcarbonyloxy)androst-4-en-19-al.

The compounds of general Formulas I to V can be used alone or suitably admixed with an appropriate pharmaceutical carrier for the purpose of inducing an estrogenic response in a patient in need thereof with lowered incidence of side effects that commonly occur with estrogen therapy and particularly with lowered incidence of side effects upon the blood clotting systems and the uterus. In essence the compounds employed in the present invention can be used for any purpose for which estrogens or estrogenic substances have or can be used including the following: hypogonadism as substitution therapy, post-menopausal supportive therapy, infertility evaluation, correction of menstrual patterns, symptoms of menopause, atrophic vaginitis, to increase cervical mucin, post-coital contraception, breast cancer, prevention of post-partum breast enlargement, acne, aging skin, male pattern baldness, contraception in conjunction with a progestogen for ovulation suppression, osteoporosis, benign prostatic hypertrophy, hirsutism, micromastia, chemical caponization of poultry, suppression of estrus in the bitch and growth promotion in cattle.

The compounds employed in the present invention can be administered in various manners to achieve the desired estrogenic response. The compounds can be administered alone or in the form of pharmaceutical preparations to the patient being treated either orally, parenterally, that is, subcutaneously or intramuscularly, or topically. The amount of compound administered will vary with the mode of administration. For oral administration the effective amount, that is, the amount of compound effective in inducing an estrogenic response in from 0.01 mg/kg up to 3.0 mg/kg, and preferably from 0.1 mg/kg to 1.0 mg/kg. For parenteral administration, that is, subcutaneous or intramuscular administration the effective amount will vary from 0.01 mg/kg up to 1.0 mg/kg and preferably from 0.1 mg/kg to 0.5 mg/kg. For topical administration the effective amount of compound employed on a percent basis is from 0.001% to 5% and preferably from 0.005% to 1%.

For oral administration a unit dosage may contain, for example, from 10 to 100 mg of the active ingredient. For parenteral administration a unit dosage may contain, for example, from 5 to 50 mg of the active ingredient. Repetitive daily administration of the compounds may be desired and will vary with the condition of the patient and the mode of administration.

As used herein the term patient is taken to mean warm blooded animals, for example, birds, such as, chickens and turkeys, and mammals, such as, primates, humans, sheep, horses, bovine cows and bulls, pigs, dogs, cats, rats, and mice.

For oral administration the compounds can be formulated into solid or liquid preparations such as capsules, pills, tablets, troches, powders, solutions, suspensions or emulsions. The compounds can be applied in the form of an aerosol containing finely divided particles of the active ingredient or a solution, suspension or emulsion of the active ingredient. The solid unit dosage forms can be a capsule which can be of the ordinary gelatin type containing a compound of general Formula I and a carrier, for example, lubricants and inert filler such as lactose, sucrose, and corn starch. In another embodiment the compounds of general Formula I can be tableted with conventional tablet bases such as lactose, sucrose and corn starch in combination with binders such as acacia, corn starch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

For topical administration the formulated active ingredient can be applied directly to the site requiring treatment or it can be applied to a mucosal membrane such as the oral or nasal mucosa. Applicator sticks carrying the formulation may be employed in administering the compounds. The topical formulation can be, for example, in the form of a solution, suspension, emulsion, gel or cream of either the oil in water or water in oil type, ointment, paste, jelly, paint or powder. Suitable bases for the topical preparation may be of any conventional type such as oleaginous bases, for example, olive oil, cottonseed oil, petrolatum, white petrolatum, mineral oils, silicones, such as, dimethylpolysiloxane or methyl phenylpolysiloxane, lanolins, polyethylene glycol, glyceryl monostearate, methyl cellulose and hydroxy methyl cellulose. The topical formulation may contain pharmaceutically acceptable surfactants, wetting agents, dispersing agents, emulsifiers, penetrants, emollients, detergents, hardeners, preservatives, fillers, antioxidants, perfumes, cooling agents, such as, menthol, smoothing agents, such as, camphor, or coloring agents, such as zinc oxide. Aerosol preparations of a solution, suspension or emulsion containing the active ingredient or an aerosol containing the active ingredient in the form of a finely ground powder can also be employed for topical administration. The aerosols may be packaged in a pressurized aerosol container together with a gaseous or liquified propellant, for example, dichlorodifluoromethane, dichlorodifluoromethane with dichlorodifluoroethane, carbon dioxide, nitrogen, or propane with the usual adjuvant such as cosolvent and wetting agents as may be necessary or desirable. The compounds may also be administered in a nonpressurized form such as in a nebulizer or atomizer.

Following are illustrative pharmaceutical formulations which may be employed in practicing the present invention:

| Solution | |
|---|---|
| 3,17-Dioxoandrost-4-en-19-al | 0.85 g |
| Alcohol | 78.9 ml |
| Isopropyl Myristate | 5.0 g |
| Polyethylene Glycol 400 | 10.0 g |
| Purified Water qs ad | 100 ml |

Combine the alcohol, isopropyl myristate and polyethylene glycol 400 and dissolve the drug substance therein. Add sufficient purified water to give 100 ml.

| A Gel | |
|---|---|
| 3,17-Dioxoandrost-4-en-19-al | 0.85 g |
| Alcohol | 78.9 ml |
| Isopropyl Myristate | 5.0 g |
| Polyethylene Glycol 400 | 10.0 g |
| Carbopol 940 (Carboxypolymethylene) | 0.75 g |
| Triethylamine | qs |
| Purified Water qs ad | 85 g |

Disperse the Carbopol 940 in the isopropyl myristate. To 38 ml of alcohol add 7 ml of purified water and the polyethylene glycol 400 and mix. Combine the two phases and nix until well dispersed. Add sufficient triethylamine to give a neutral pH. Dissolve the drug substance in the balance of the alcohol and mix well into the barch. Add and mix sufficient purified water to provide 85 g of finished product.

| Applicator Stick | |
|---|---|
| 3,17-Dioxoandrost-4-en-19-al | 0.85 g |
| Absolute Alcohol | 75 ml |
| Polyethylene Glycol 400 | 10.0 g |
| Isopropyl Myristate | 5.0 g |
| Stearic Acid | 4.3 g |
| Sodium Hydroxide | 0.55 g |
| Purified Water qs ad | 85 g |

Combine the absolute alcohol, polyethylene glycol 400 and isopropyl myristate and dissolve the drug substance therein. Add the stearic acid and heat the mixture to about 65° C. Dissolve the sodium hydroxide in a small amount of water, add and mix. Add sufficient water to provide 85 g of finished product. Pour into suitable moulds and allow to solidify.

| Aerosol Foam | |
|---|---|
| 3,17-Dioxoandrost-4-en-19-al | 1.0 g |
| Propylene Glycol | 96.0 g |
| Emulsifying Wax NF XIV | 3.0 g |
| Dichlorodifluoromethane:cryofluorane (20:80) | 6.9 g |

Dissolve the drug substance in the propylene glycol. Add the emulsifying wax and heat to approximately 70° C. Stir while cooling to room temperature. Charge a suitable aerosol unit with this concentrate and 6.9 g of dichlorodifluoromethane:cryofluorane (20:80).

| Tablet | For 15,000 |
|---|---|
| 3,17-Dioxoandrost-4-en-19-al Fine Powder | 75 g |
| Lactose | 1.216 Kg |
| Corn Starch | 0.3 Kg |

Mix the active ingredient, the lactose and corn starch uniformly. Granulate with 10% starch paste. Dry to a moisture content of about 2.5%. Screen through a No. 12 mesh screen. Add and mix the following:

| Magnesium Stearate | 0.015 Kg |
|---|---|
| Corn Starch qs ad | 1.725 Kg |

Compress on suitable tablet machine to a weight of 0.115 g/tablet.

| Soft Gelatin Capsule | |
|---|---|
| 3,17-Dioxoandrost-4-en-19-al | 0.25 Kg |
| Polysorbate 80 | 0.25 Kg |
| Corn Oil qs ad | 25.0 Kg |

Mix and fill into 50,000 soft gelatin capsules.

| IM Depot Injection | |
|---|---|
| Each 1 ml contains the following: | |
| 3,17-Dioxoandrost-4-en-19-al | 5.0 mg |
| Anhydrous Chlorobutanol | 5.0 mg |
| Aluminum Monostearate | 50.0 mg |
| Peanut Oil qs ad | 1.0 ml |

Dissolve or disperse the ingredients in the peanut oil.

| Depot - Implant | |
|---|---|
| 3,17-Dioxoandrost-4-en-19-al micronized | 5 mg |
| Dimethylsiloxane | 240 mg |
| Catalyst qs | |

Disperse the drug substance in the fluid dimethylsiloxane. Add the catalyst and cast into a suitable monolytic structure.

Alternatively, the drug substance may be enclosed by a pre-case polydimethylsiloxane envelope.

Alternatively, the drug substance may be dispersed in a suitable amount of hydroxyethyl acrylate subsequently polymerized and cross-linked by the addition of ethylenedimethacrylate, and an oxidizing agent, to yield a 3-dimensional ethylene glycomethacrylate mouldable gel (Hydron).

| Topical Cream, Vanishing, o/w | |
|---|---|
| | % w/w |
| 3,17-Dioxoandrost-4-en-19-al | 1 |

| Topical Cream, Vanishing, o/w -continued | |
|---|---|
| | % w/w |
| Stearic Acid | 15 |
| Isopropyl Myristate | 2 |
| Sorbitan Monostearate | 1.8 |
| Polyoxyethylene Sorbitan Monostearate | 2.3 |
| Propylene Glycol | 5 |
| Methylparaben | 0.025% |
| Propylparaben | 0.015% |
| Purified Water | qs |

| IM Injections | | |
|---|---|---|
| A. | Oil Type: | |
| | 3,17-Dioxoandrost-4-en-19-al | 25 mg |
| | BHA, BHT aa | 0.01% w/v |
| | Peanut Oil or Sesame Oil qs | 1.0 ml |
| B. | Suspension Type: | |
| | 3,17-Dioxoandrost-4-en-19-al micronized | 25 mg |
| | Sodium Carboxymethylcellulose | 0.5% w/v |
| | Sodium Bisulfite | 0.02% w/v |
| | Water for Injection, qs | 1.0 ml |

| Buccal or Sublinqual Tablet | |
|---|---|
| 3,17-Dioxoandrost-4-en-19-al | 1% |
| Calcium Stearate | 1% |
| Calcium Saccharin | 0.02% |
| Granular Mannitol | qs |

Mix and compress on a suitable tablet machine to a weight of 0.115 g/tablet.

| Powder | |
|---|---|
| | % w/w |
| 3,17-Dioxoandrost-4-en-19-al micronized | 1 |
| Silicon dioxide, anhydrous | 0.5 |
| Corn starch, lactose, fine powder aa | qs |

| Oleaginous Ointment | |
|---|---|
| | % w/w |
| 3,17-Dioxoandrost-4-en-19-al | 1 |
| White wax | 5 |
| White petrolatum qs | 100 |

| Absorption Ointment Base | |
|---|---|
| 3,17-Dioxoandrost-4-en-19-al | 1 |
| Cholesterol | 3 |
| Stearyl alcohol | 3 |
| White wax | 8 |
| White petrolatum qs | 100 |

| Water Soluble Ointment Base | |
|---|---|
| | % w/w |
| 3,17-Dioxoandrost-4-en-19-al | 1 |
| Polyethylene glycol 4000 | 40 |
| Polyethylene glycol 400 qs | 100 |

| Paste | |
|---|---|
| | % w/w |
| 3,17-Dioxoandrost-4-en-19-al | 1 |
| Starch | 25 |
| Zinc oxide | 25 |

| -continued | |
|---|---|
| Paste | |
| | % w/w |
| White petrolatum qs | 100 |

Medicated Tampon 50 mg of 3,17-dioxoandrost-4-en-19-al in a volatile solvent, such as, ethyl alcohol is applied to a vaginal tampon of cellulosic or related composition and allowed to dry therein.

| Donor Pessary | |
|---|---|
| 3,17-Dioxoandrost-4-en-19-al | 50 mg |
| Dimethylsiloxane | 5 g |
| Catalyst, suitable | qs |

Disperse the active ingredient in the fluid dimethylsiloxane, add the catalyst and cast into a suitable structure for vaginal insertion, such as, a doughnut shape.

| Vaginal Cream | |
|---|---|
| | % w/w |
| 3,17-Dioxoandrost-4-en-19-al | 1.0 |
| Lactose | 5.0 |
| Lactic Acid, 50% | 1.3 |
| Sorbitol Solution, 70% | 15.0 |
| Stearic Acid | 10.0 |
| Diglycol Stearate | 7.0 |
| Polysorbate 80 USP | 1.0 |
| Benzoic Acid | 0.1 |
| Purified Water | qs |

| Vaginal Insufflation Powder | |
|---|---|
| | % w/w |
| 3,17-Dioxoandrost-4-en-19-al, micronized | 1% |
| Silicon Dioxide Anhydrous | 0.5% |
| Corn Starch and Lactose, Fine Powder | qs (of each) |

When the compounds employed in the present invention are used to effect a contraceptive result by inhibition of ovulation or suppression of ovulation the compounds can be used alone or in combination with a progestogen. Suitable progestogens for use are norethindrone, norethindrone acetate, norethynodrel, lynestrenol, ethynodioldiacetate, quingestanol, algestone acetophenide, medroxyprogesteroneacetate, megestrol acetate, melengestrol acetate, dimethisterone, norgestrel and dydrogesterone. As ovulation inhibitors the compounds of general Formula I can be used alone for contraception or by administering said compounds on from day five to day twenty-one of the cycle. When the compounds of general Formula I are used for contraception in combination with a progestogen the compounds of general Formula I and the progestogen can be administered together on from day 5 to day 21 of the cycle, or the compounds of general Formula I can be administered on from day 5 to day 21 and the progestogen administered on from day 16 to day 21 of the cycle.

As used herein the term symptoms of menopause is taken to mean the symptoms which occur in the menopause or postmenopausal women including hot flashes, or hot flushes, inappropriate or excessive perspiration, atrophic vaginitis, changes in the skin, primarily wrinkling through dehydration of the skin, particularly exposed facial skin and a thinning of the epidermis and loss of rete ridges, and post-menopausal osteoporosis or osteopenia.

Following are illustrative formulations for use when the compounds of general Formula I are used in combination with a progestogen for ovulation inhibition:

| Aerosol Foam | |
|---|---|
| 3,17-Dioxoandrost-4-en-19-al | 1.0 g |
| Norethindrone | 0.05 g |
| Propylene glycol | 96 g |
| Emulsifying Wax NF XIV | 3.0 g |
| Dichlorodifluoromethane:Cryofluorane (20:80) | 6.9 g |

Dissolve the drug substance in the propylene glycol. Add the emulsifying wax and heat to approximately 70° C. Stir while cooling to room temperature. Charge a suitable aerosol unit with this concentrate and 6.9 g of dichlorofluoromethane:cryofluorane (20:80).

| IM Depot Injection | |
|---|---|
| Each 1 ml contains the following: | |
| 3,17-Dioxoandrost-4-en-19-al | 5.0 mg |
| Norethindrone | 0.05 mg |
| Anhydrous chlorobutanol | 5.0 mg |
| Aluminum monostearate | 50.0 mg |
| Peanut oil qs ad | 1.0 ml |

Dissolve or disperse the ingredients in the peanut oil.

When the compounds of general Formula I are used to treat benign prostatic hypertrophy or prostatic carcinoma higher dosage amounts than indicated hereinabove may be employed, for example, from about 0.1 to about 500 mg/kg, and preferably from about 0.1 to 250 mg/kg, which amounts will provide a method of treatment wherein the potential for the occurrence of thrombotic effects is less than with estrogen treatment.

The following data demonstrate that the compounds of general Formula I are effective in inducing an estrogenic response.

To demonstrate the anti-acne and anti-seborrheic activity of the compounds employed in the present invention ovariectomized rats which has been implanted with testosterone to induce sebum secretion were treated subcutaneously with 3 $\mu$g per day per rat of either estradiol or 3,17-dioxoandrost-4-en-19-al for 20 days. On the eighteenth day of treatment the rats were washed to remove lipid secretions from the hair. The amount of lipids secreted in the subsequent 48 hours was determined by the method of Ebling and Skinner, Brit. J. Dermatol. 92, 321-4 (1975). The results are summarized in the following Table I and indicate that 3,17-dioxoandrost-4-en-19-al was as effective as, if not better than, estradiol in decreasing sebum production.

TABLE I

| | Anti-Seborrheic Activity | |
|---|---|---|
| Treatment | Dose $\mu$g/rat/day | Sebum production mg/g hair-48 hrs. |
| Testosterone implant control | — | 1.38 ± 0.28 |
| Testosterone implant plus estradiol | 3.0 | 0.21 ± 0.23* |
| Testosterone implant plus 3,17-dioxoandrost-4-en-19-al | 3.0 | −0.09 ± 0.25* |

*Significantly different from control, $p \leq 0.001$

To demonstrate the ovulation inhibitory effect of the compounds of general Formula I immature female SpragueDawley rats were treated daily on the nineteenth through the twenty-fourth day of age with various dosage concentrations of a compound of general Formula I. On the twenty-second day of age each rat was injected with two international units of a gonadotrophin, for example, pregnant mare's serum to induce ovulation. The number of ova present in the oviduct was determined on the morning of the twenty-fifth day. The following tabulation shows the effect of 3,17-dioxoandrost-4-en-19-al in this test system.

| | Ovulation-Inhibition | | | |
|---|---|---|---|---|
| Treatment | Dose (mg/day) | No. Rats | % Ovulating | Total No. Ova |
| Vehicle | — | 6 | 83 | 28 |
| 3,17-Dioxoandrost-4-en-19-al | 1.0 | 6 | 33 | 6* |

*Significantly different from vehicle treated control, $p \leq 0.05$

To demonstrate the activity of the compounds employed in the present invention immature intact male SpragueDawley rats 23 days of age were treated parenterally with the test compound for ten days. The drug effect on gonadal accessory organs was demonstrated by determining the relative organ weight on the eleventh day of treatment. When 3,17-dioxoandrost-4-en-19-al is administered as the test compound ventral prostate weight was significantly reduced when compared with vehicle treated controls as demonstrated by the data contained in the following Table I.

TABLE I

| | Inhibition of Prostatic Growth | | | |
|---|---|---|---|---|
| Treatment | mg/kg-day | No. Rats | Prostate Wgt.* (mg ± S.E.M.) | % of Control |
| Vehicle | — | 10 | 67.5 ± 5.4 | 100 |
| 3,17-Dioxo-androst-4-en-19-al | 50 | 6 | 40.0 ± 4.4* | 59 |

*Relative organ weight, mg/100 g body weight
**Significantly different from vehicle controls, $p \leq 0.01$ The effectiveness of the compounds employed herein has also been demonstrated in dogs. An aged beagle dog was diagnosed by way of rectal palpation to have an enlarged prostate. Pathological examination of a pretreatment prostate biopsy confirmed hyperplasia and prostatitis. Dimethylpolysiloxane implants containing micronized crystalline 3,17-dioxoandrost-4-en-19-al prepared to deliver an estimated 300 to 500 μg/24 hours were implanted. After seven months of therapy a second prostatic biopsy was performed at which time the prostate was approximately one-fourth the size seen at the first examination and neither prostatitis nor hyperplasic cells were seen in the tissues examined confirming the effectiveness of the compound.

That the compounds of general Formula I can be used without the occurrence of deleterious estrogenic side effects is demonstrated by the following data:

The data contained in the following Table II indicate that 3,17-dioxoandrost-4-en-19-al does not bind in vitro with the estrogen receptor of uterine estrogen target tissue. This binding is the first step necessary for hormonal action. To obtain these data female hamsters were ovariectomized and uterine cytosol was prepared 24 to 48 hours post surgery. Concentrations of $4 \times 10^{-6}$ to $4 \times 10^{-10}$ molar were compared for competitive bindings of $H^3$-estradiol-17β-labeled cytosol receptor sites according to the methods of Leavitt et al., Endocrin. 94, 1041 (1974) and Korenman, J. Clin. Endocrin. and Metab. 28, 127 (1968). The relative binding was compared with estradiol which was equated to 100.

TABLE II

| | Uterine Cytosol Affinity |
|---|---|
| Treatment | Relative Estrogen Binding Affinity |
| Estradiol | 100 |
| Estrone | 22 |
| Estriol | 10 |
| 3,17-Dioxoandrost-4-en-19-al | 0.01 |

The lack of estrogen binding affinity of 3,17-dioxoandrost-4-en-19-al supports the finding of lack of certain estrogenic side effects of the compounds employed in the present invention.

That the compounds employed in the present invention have no significant uterotrophic effect as compared to estradiol is reflected by the data in the following Table III which were generated from ovariectomized rats treated with 3 μg per rat per day of either estradiol of 3,17-dioxoandrost-4-en-19-al for 20 days.

TABLE III

| | Uterotrophic Activity | |
|---|---|---|
| Treatment | Dose (μg/rat) | Uterine Wt. (mg ± S.E.M.) |
| Control | — | 33.7 ± 1.7 |
| Estradiol | 3.0 | 206.6 ± 8.1* |
| 3,17-Dioxoandrost-4-en-19-al | 3.0 | 41.1 ± 4.7 |

*Significantly different from control; $p \leq 0.01$

The data contained in Tables I and III demonstrate that 3,17-dioxoandrost-4-en-19-al has a selective effect on sebum production without a systemic estrogenic effect on uterine weight or vaginal cornification which occurs with estradiol treatment.

It has also been found that the compounds employed in the present invention have no thrombotic potential. For example, 3,17-dioxoandrost-4-en-19-al was given subcutaneously to ovariectomized albino rats for seven days at either 0.1 or 3.0 mg/kg. Body weight and uterine weights were measured. Blood samples were taken and the effect on thrombotic potential determined through measurements of anti-thrombin III activity, ethanol gel tests, (fibrin monomer level), protamine sulfate test (fibrin degradation products), adenosinediphosphate and collagen induced platelet aggregation. Anti-thrombin activity was not affected nor was increased fibrin monomer or fibrin degradation product level detected. Platelet aggregation was not significantly changed.

Many of the compounds employed in the present invention are known in the art or are commercially available. For example, 19-hydroxyandrost-4-ene-3,17-dione, 17β,19-dihydroxyandrost-4-en-3-one, 19-hydroxy-17β-(1-oxoethoxy)androst-4-en-3-one, 19-hydroxy-17β-(1-oxobenzyloxy)androst-4-en-3-one and 3-oxo-17β-(1-oxobenzyloxy)androst-4-en-19-al are commercially available.

The esters of the compounds employed in the present invention, that is, compounds wherein either or both of $R_1$ and $R_2$ are alkylcarbonyl wherein the alkyl moiety has from 1 to 20 carbon atoms and is straight or branched, cycloalkylcarbonyl wherein the cycloalkyl moiety has from 5 to 10 carbon atoms, benzoyl and phenylalkylcarbonyl wherein the alkyl moiety has from 1 to 6 carbon atoms and is straight or branched can be prepared as follows although other methods may also be employed. Ester derivatives of 19-hydroxyandrost-4-ene-3,17-dione and bis-ester derivatives of 17β,19-hydroxyandrost-4-en-3-one are prepared by reacting the corresponding 19-hydroxy or 17β,19-dihydroxy compound with an appropriate acid anhydride of the formula

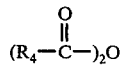

or acid chloride of the formula

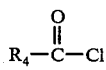

wherein $R_4$ is an alkyl group of from 1 to 20 l carbon atoms and is straight or branched, a cycloalkyl group of from 5 to 10 carbon atoms, phenyl or phenylalkyl wherein the alkyl moiety has from 1 to 6 carbon atoms and is straight or branched in the presence of a base such as pyridine, quinoline or trialkylamine, such as, triethylamine, which base serves as the solvent, for from 1 to 24 hours at a temperature of from about 25° C to 100° C. The appropriate acid anhydride or acid chloride are known in the art or can be prepared from the corresponding acids by procedures well known in the art.

Compounds employed in the present invention wherein $R_1$ is hydrogen and $R_2$ forms an ester group are prepared from the above obtained 17β,19-diester derivatives by refluxing the diester with one equivalent of sodium bicarbonate or potassium bicarbonate or one-half equivalent of sodium carbonate or potassium carbonate or dilute sodium hydroxide or potassium hydroxide solution in a lower alcohol solvent such as methanol or ethanol and water for about one hour, the reflux temperature depending on the solvent system employed.

Compounds employed in the present invention wherein R is CHO and $R_2$ forms an ester group are prepared by dissolving the above obtained compounds wherein $R_1$ is hydrogen and $R_2$ forms an ester group in acetone cooled to 0 to 10° C and treating the solution with sufficient Jones reagent to effect the oxidation. Jones reagent is prepared by standard procedures using 26.72 grams of chromium trioxide, 23 ml of concentrated sulfuric acid and water to make 100 ml. The Jones reagent can be added to the solution until the reddish brown color persists which requires about 289 ml. Other oxidizing agents can be used, such as, dicyclohexylcarbodiimide in dimethylsulfoxide.

The following specific examples further illustrate the preparation of compounds employed in the instant invention.

EXAMPLE 1

17β,19-Bis(1-oxopropoxy)androst-4-en-3-one

A solution of 10 g of 17β,19-dihydroxyandrost-4-en-3-one which is commercially available and 25 ml of propionic anhydride in 200 ml of pyridine is allowed to stand overnight after which 100 ml of ethanol is added, and the reaction mixture is stirred for one hour. The mixture is then poured into 1 liter of water and the solid product is collected by filtration. The solid is dissolved in ether, dried over magnesium sulfate, filtered and the solvent removed. The residue is dissolved in hot hexane and allowed to cool yielding 17β,19-bis(1-oxopropoxy)-androst-4-en-3-one. M.P. 82°–84° C.

EXAMPLE 2

17β,19-Dihydroxyandrost-4-en-3-one

A solution of 150 g of 19-hydroxyandrost-4-en-3-one in 6 liters of ethanol is cooled in an ice bath. To this cold solution is added 13.5 g of potassium borohydride, and the reaction mixture is stirred for 2 hours at about 0° C after which a second 13.5 g or potassium borohydride is added. Two hours later a third 13.5 g portion of potassium borohydride is added to the reaction mixture which is stirred for an additional 1 hour then poured into 11 liters of water to which 70 ml of acetic acid is added. The ethanol is distilled off under reduced pressure and the aqueous residue cooled to 0° C. The solid which separates is filtered off, dried and dissolved in 25 liters of hot chloroform after which the temperature is adjusted to 25° C. To the chloroform solution is added 250 g of manganese dioxide, and the mixture is stirred for 2 hours then filtered and the solvents removed under reduced pressure. The solid residue is recrystallized from acetonitrile to give 17β,19-dihydroxyandrost-4-en-3-one. M.P. 205°–207° C.

EXAMPLE 3

19-Hydroxy-17β(1-oxopropoxy)androst-4-en-3-one

A solution of 11 g of 17β,19-bis(1-oxopropoxy)androst-4-en-3-one in 2 liters of methanol is treated with 2.5 g of sodium carbonate in 250 ml of water and refluxed for 1 hour after which the reaction mixture is poured into 10 liters of water, and the solid collected by filtration. The solid is dissolved in methylene chloride, dried over magnesium sulfate, filtered and the solvent removed. The residue is crystallized from acetone-hexane yielding 6 g of 19-hydroxy-17β(1-oxopropoxy)androst-4-en-3-one. M.P. 160°–162° C.

EXAMPLE 4

19-Acetoxyandrost-4-ene-3,17-dione

A solution of 19-hydroxyandrost-4-ene-3,17-dione in acetic anhydride and pyridine is allowed to stand overnight after which the reaction mixture is poured into ice water. The resulting solid is collected, dried and recrystallized from hexane to give 19-acetoxyandrost-4-ene-3,17-dione.

EXAMPLE 5

19-Acetoxy-17β-hydroxyandrost-4-en-3-one

To a solution of 25.6 g of 19-acetoxyandrost-4-ene-3,17-dione in 4 liters of methanol cooled to 0° C is added 3.1 g of sodium borohydride, and the mixture is stirred at 0° C for 1 hour after which 30 ml of acetic acid is added and the methanol removed under reduced pressure. The resulting residue is taken up in ethyl acetate and washed with water. The organic layer is dried over magnesium sulfate, filtered and the solvent removed. The solid residue is dissolved in 2 liters of chloroform treated with 125 g of manganese dioxide and stirred for two hours. The reaction mixture is filtered, and the solvent removed under reduced pressure. The residue is chromatographed on alumina using benzene-ether (1:1) as the eluant. The product is recrystallized from acetone-hexane to give 19-acetoxy-17β-hydroxyandrost-4-en-3-one, M.P. 125°–127° C.

EXAMPLE 6

19-Hydroxy-17β(2'-tetrahydropyranyloxy)androst-4-en-3one

To a solution of 10 g of 19-acetoxy-17β-hydroxyandrost-4-en-3-one in 300 ml of dihydropyran is added a small crystal of p-toluene sulfonic acid. The reaction mixture is allowed to stand overnight after which it is dissolved in ether and extracted with dilute sodium bicarbonate. The ether layer is dried over magnesium sulfate, filtered and the solvent removed. The resulting residue is dissolved in 2 liters of methanol and 2.5 g of sodium bicarbonate in 250 ml of water is added. The methanol solution is refluxed for 1 hour after which the solvent is removed under reduced pressure at 40° C. The residue is covered with water, and the solid crude product collected and recrystallized from ethylacetate yielding 19-hydroxy-17β(2'-tetrahydropyranyloxy)androst-4-en-3-one. M.P. 193°–199° C.

EXAMPLE 7

3-Oxo-17β-hydroxyandrost-4-en-19-al

A solution of 7 g of 19-hydroxy-17β(2'-tetrahydropyranyloxy)androst-4-en-3-one in 500 ml of acetone is cooled to 10° C and 5.3 ml of Jones reagent is added dropwise. The reaction is stirred for an additional 10 minutes then poured into water and extracted with ethyl-acetate. The ethylacetate extract is dried over magnesium sulfate, filtered and the solvent removed under reduced pressure. The residue is dissolved in 250 ml of 95% ethanol and 2 ml of concentrated hydrochloridic acid is added. The ethanol solution is refluxed for one hour then cooled to room temperature and neutralized with solid sodium carbonate. The neutralized solution is diluted with water and extracted with ethyl acetate. The extract is dried over magnesium sulfate, filtered and the solvent removed leaving a residue which is chromatagraphed on alumina using 25% ether in benzene as the eluant to give the product 3-oxo-17β-hydroxyandrost-4-en-19-al, M.P. 125°–127° C.

EXAMPLE 8

19-(1-Adamantanylcarbonyloxy)androst-4-ene-3,17-dione

A solution of 22 g of 19-hydroxyandrost-4-ene-3,17-dione, 18 g of 1-adamantanecarboxylic acid chloride, and 29 ml of pyridine in 2.2 liters of toluene is refluxed overnight. The reaction mixture is cooled, and the toluene layer is washed with water, dried over magnesium sulfate and filtered then the solvent is removed. The resulting residue is crystallized from methanol to give 19-(1-adamantanylcarbonyloxy)androst-4-ene-3,17-dione, M.P. 161°–163° C.

EXAMPLE 9

3,17-Dioxoandrost-4-en-19-al

To a solution of 30 g of 19-hydroxyandrost-4-ene-3,17-dione in 3 liters of acetone cooled in an ice bath is added 28 ml of Jones reagent over a 1 hour period. The reaction mixture is stirred for an additional fifteen minutes, filtered and the solvent removed under reduced pressure at 35° C. The residue is taken up in a large volume of ether and 1.5 liters of water. The ether layer is collected, dried over magnesium sulfate, filtered and the solvent removed. The residue is crystallized from acetone-hexane to give 3,17-dioxoandrost-4-en-19-al, M.P. 126°–129° C.

EXAMPLE 10

3-Oxo-17β-(1-oxopropoxy)androst-4-en-19-al

To a solution of 14 g of 19-hydroxy-17β-(1-oxopropoxy)androst-4-en-3-one in 1 liter of acetone cooled in an ice bath is added 13.3. ml of Jones reagent over 1 hour after which the reaction mixture is poured into a large volume of water and extracted with ether. The ether extract is dried over magnesium sulfate, filtered and the solvent removed. The residue is crystallized from acetone-hexane to give 3-oxo-17β(1-oxopropoxy)-androst-4-en-19-al, M.P. 119°–121° C.

We claim:

1. A method of inducing an estrogenic response in a patient in need thereof which comprises administering to said patient a compound of the formula in an amount effective to induce an estrogenic response:

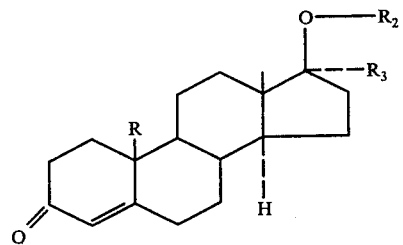

wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$ and R$_3$ together form a double bond between the 17- position carbon atom and the oxygen atom; and a pharmaceutically acceptable carrier.

2. The method of claim 1 wherein R is —CHO.

3. The method of claim 2 wherein R$_2$ and R$_3$ together form a double bond between the 17- position carbon atom and the oxygen atom.

4. The method of claim 3 wherein the compound is 3,17-dioxoandrost-4-en-19-al.

5. The method of claim 1 wherein R is —CH$_2$OR$_1$.

6. The method of claim 5 wherein R$_2$ and R$_3$ together form a double bond between the 17- position carbon atom and the oxygen atom.

7. The method of claim 6 wherein the compound is 19-hydroxyandrost-4-en-3,17-dione.

* * * * *

UNITED STATES PATENT AND TRADEMARK OFFICE
CERTIFICATE OF CORRECTION

PATENT NO. : 4,078,060
DATED : March 7, 1978
INVENTOR(S) : H.D. Benson, J.F. Grunwell, J.O. Johnston and V. Petrow It is certified that error appears in the above-identified patent and that said Letters Patent are hereby corrected as shown below:

Column 2, line 30 ...of the structure alkyl 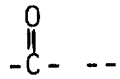

should read "of the structure alkyl-$\overset{\overset{O}{\|}}{C}$-". Column 6, line 8 ...smoothing... should read "soothing"; line 48 ...nix... should read "mix". Column 8, line 25 ...sublinqual... should read "sublingual"; line 42 ...oleaqinous... should read "oleaqinous". Column 13, line 17 ...20 1 carbon... should read "20 carbon".

Signed and Sealed this

Ninth Day of January 1979

[SEAL]

Attest:

RUTH C. MASON
Attesting Officer

DONALD W. BANNER
Commissioner of Patents and Trademarks